US009024037B1

(12) United States Patent
Tan et al.

(10) Patent No.: US 9,024,037 B1
(45) Date of Patent: May 5, 2015

(54) TWO-PHOTON ABSORBING POLYMERS BASED ON TRIARYLAMINE-BENZOBISTHIAZOLE-TRIARYLAMINE QUADRUPOLAR-STRUCTURE MOTIF

(75) Inventors: Loon-Seng Tan, Centerville, OH (US); Ramamurthi Kannan, Cincinnati, OH (US); Matthew Dalton, Bellbrook, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 204 days.

(21) Appl. No.: 13/475,187

(22) Filed: May 18, 2012

Related U.S. Application Data

(60) Provisional application No. 61/487,774, filed on May 19, 2011.

(51) Int. Cl.
*C07D 513/02* (2006.01)
*H01L 51/00* (2006.01)

(52) U.S. Cl.
CPC ........ *H01L 51/0036* (2013.01); *H01L 51/0059* (2013.01); *C08G 2261/91* (2013.01); *C08G 2261/3142* (2013.01)

(58) Field of Classification Search
CPC .................. C08G 2261/3142; C08G 2261/91; C08G 2261/3162; H01L 51/0059
USPC ...................... 528/37; 548/150, 151, 153, 158
See application file for complete search history.

(56) References Cited

U.S. PATENT DOCUMENTS

| | | | |
|---|---|---|---|
| 3,455,879 A | 7/1969 | Gay et al. | |
| 3,600,361 A | 8/1971 | Heacock et al. | |
| 3,732,200 A | 5/1973 | Bach | |
| 3,835,120 A | 9/1974 | Bach | |
| 5,521,277 A | 5/1996 | Tan et al. | |
| 5,534,613 A | 7/1996 | Tan et al. | |
| 5,585,217 A | 12/1996 | Oba | |
| 5,633,337 A | 5/1997 | Tan et al. | |
| 5,770,737 A | 6/1998 | Reinhardt et al. | |
| 6,001,277 A | 12/1999 | Ichimura et al. | |
| 6,100,405 A | 8/2000 | Reinhardt et al. | |
| 6,300,502 B1 | 10/2001 | Kannan et al. | |
| 6,300,793 B1 | 10/2001 | Ting et al. | |
| 6,538,098 B1 | 3/2003 | Goldfinger | |
| 6,555,682 B1 | 4/2003 | Kannan et al. | |
| 6,680,016 B2 | 1/2004 | Wang et al. | |
| 6,696,142 B2 | 2/2004 | Baer et al. | |
| 6,730,793 B1 * | 5/2004 | Kannan et al. | 548/150 |
| 6,849,707 B1 | 2/2005 | Baek et al. | |
| 6,867,304 B1 | 3/2005 | Tan et al. | |
| 6,974,857 B1 | 12/2005 | Baek et al. | |
| 7,005,550 B1 | 2/2006 | Tan et al. | |
| 7,026,432 B2 | 4/2006 | Charati et al. | |
| 7,067,674 B1 | 6/2006 | Kannan et al. | |
| 7,319,151 B1 | 1/2008 | Tan et al. | |
| 7,807,127 B1 | 10/2010 | Forohar et al. | |
| 7,960,471 B1 | 6/2011 | Tan et al. | |
| 8,173,763 B1 | 5/2012 | Tan et al. | |
| 8,318,888 B1 | 11/2012 | Tan et al. | |
| 8,471,035 B1 * | 6/2013 | Tan et al. | 548/151 |
| 8,546,614 B1 | 10/2013 | Tan et al. | |
| 8,580,958 B1 | 11/2013 | Tan et al. | |
| 8,674,057 B1 | 3/2014 | Tan et al. | |
| 8,728,861 B2 | 5/2014 | Bayraktaroglu et al. | |
| 8,895,730 B2 | 11/2014 | Tan et al. | |
| 2004/0233377 A1 | 11/2004 | Utsumi et al. | |
| 2007/0052350 A1 | 3/2007 | Su et al. | |
| 2010/0102761 A1 | 4/2010 | Von Malm et al. | |
| 2011/0108813 A1 | 5/2011 | Kohiro et al. | |

FOREIGN PATENT DOCUMENTS

| | | |
|---|---|---|
| EP | 2380867 | 10/2011 |
| GB | 1147856 | 5/2005 |
| JP | 2005154643 | 6/2005 |

OTHER PUBLICATIONS

REAXYSFILE on STN CAS ONLINE, Accession No. 11872719 (entry date Jun. 18, 2008).*
Tan et al Poster presentation at "9th International Symposium on Functional Pi-Electron Systems" Conference, Georgia Institute of Technology, Atlanta, GA, May 23-28, 2010).*
H. Peng et al., "Green and highly efficient functionalization of carbon nanotubes by combination of 1,3-dipolar cycloaddition and Curtius rearrangement reactions," Chinese J. Chem., vol. 28 (2010) 1223-1228.
L-S. Tan et al., Unpublished U.S. Appl. No. 10/963,469, filed Oct. 12, 2004, 15 pages total.
J. R. Smith et al., "Space durable polymer/carbon nanotube films for electrostatic charge mitigation," Polymer, vol. 45 (2004) 825-835.
H. Kong et al., "Controlled functionalization of multiwalled carbon nanotubes by in situ atom transfer radical polymerizations," JACS., vol. 126 (2004) 412-413.
J.-B Baek et al., "Improvded syntheses of Poly(oxy-1,3-phenylenecarbonyl-1,4-phenylene) and related poly(ether-keontes) using polyphosphoric acid/P2O5 as polymerization medium," Polymer, vol. 44 (2003) 4135-4137.
J. L. Bahr et al., "Covalent chemistry of single-wall carbon nanotubes," J. Mater. Chem., vol. 12 (2002) 1952-1958.
K. A. Watson et al., "Polyimide/carbon nanotube composite films for potential space applications," Int'l SAMPE Tech. Conf., vol. 33 (2001) 1551-1560.
B. Maruyama et al., "Carbon nanotubes and nanofibers in composite materials," J. SAMPE., vol. 38, (2002) 59-70.
M.S.P. Shaffer et al., "Polystyrene granted multi-walled carbon nanotubes," Chem. Commun. (2002) 2074-2075.
C. Park et al., "Dispersion of single wall carbon nanotubes by in-situ polymerization under sonication," Chem. Phys. Lett., vol. 364 (2002) 303-308.

(Continued)

*Primary Examiner* — Gregory Listvoyb
(74) *Attorney, Agent, or Firm* — AFMC LO/JAZ; Chastity Whitaker

(57) ABSTRACT

Diphenylamine-benzobisthiazole-diphenylamine monomers having two-photon absorption cross-sections and high solubility in organic solvents are provided. Also provided are the corresponding organo-soluble, wholly conjugated and two-photon absorbing benzobisthiazole-triarylamine polymers.

9 Claims, No Drawings

(56) References Cited

OTHER PUBLICATIONS

N. Tagmatarchis et al., "Sidewall functionalization of single-walled carbon nanotubes through electrophilic addition," Chem. Commun. (2002) 2010-2011.
United States Patent and Trademark Office, Non-Final Office Action in related U.S. Appl. No. 10/963,469, mailed Sep. 26, 2007, 7 pages total.
United States Patent and Trademark Office, Final Office Action in related U.S. Appl. No. 10/963,469, mailed Apr. 8, 2008, 9 pages total.
Y. Iwakura et al., "Syntheses of aromatic polyketones and aromatic polamides," J. Polymer Sci., vol. 6 (1968) 3345-3355.
United States Patent and Trademark Office, Advisory Action in related U.S. Appl. No. 10/963,469, mailed Jul. 2, 2008, 6 pages total.
A. Ambrosio et al., "Two-photon patterning of a polymer containing Y-shaped azochromophores," Appl. Phys. Lett., vol. 94 (2009) 011115-1 to 011115-3.
D-S Won et al., "Synthesis and nonlinear optical properties of a novel polyurethane containing cyanovinylthiophene with enhanced thermal stability of dipole alignment for electro-optic applications," Polym. Int., vol. 59 (2010)162-168.
United States Patent and Trademark Office, Final Office Action in related U.S. Appl. No. 13/239,606, mailed Jul. 9, 2013, 9 pages total.
United States Patent and Trademark Office, Non-Final Office Action in related U.S. Appl. No. 14/047,640, mailed Dec. 16, 2013, 14 pages total.
J. E. Beecher et al., "Concurrent stabilization and imaging of a novel polymer for second harmonic generation via in situ photopolymerization," in Technical Report #14 (1994), 67 pages total.
J. E. Rogers et al., "Insight into the nonlinear absorbance of two related series of two-photon absorbing chromophores," J. Phys. Chem. A., vol. 111 (2007) 1899-1906.
M. J. Dalton et al., "Aromatic polyimides containing main-chain diphenylaminofluorene-benzothiazole motif: fluorescence quenching, two-photon properties, and exciplex formation in solid state," Macromol., vol. 44 (2011) A-M.
United States Patent and Trademark Office, Non-Final Office Action in related U.S. Appl. No. 13/632,195, mailed Oct. 18, 2013, 10 pages total.
J-B. Baek et al., "Covalent modification of vapour-grown carbon nanofibers via direct Friedel-Crafts acylation in polyphosphoric acid," J. Mater Chem., vol. 14 (2004) 2052-2056.
S. J. Jhaveri et al., "Direct three-dimensional microfabrication of hydrogels via two-photon lithography in aqueous solution," Chem. Mater., vol. 21 (2009) 2003-2006.
United States Patent and Trademark Office, Non-Final Office Action in related U.S. Appl. No. 13/239,606, mailed Mar. 28, 2013, 9 pages total.
Z Yuxia et al., "Synthesis and characterization of a novel nonlinear optical polyurethane polymer," Eur. Poly. J., vol. 37 (2001) 445-449.
United States Patent and Trademark Office, Final Office Action received in U.S. Appl. No. 14/047,460, mailed Jun. 18, 2014.
He, Guang S.; Tan, Loon-Seng; Zheng, Qingdong; Prasad, Paras N., "Multiphoton Absorbing Materials: Molecular Designs, Characterizations, and Applications", Chemical Reviews (2008), 108(4), 1245-1330.
Kevin D. Belfield, Sheng Yao, Alma R. Morales, Joel M. Hales, David J. Hagan, Eric W. Van Stryland, Victor M. Chapela, Judith Percino, "Synthesis and characterization of novel rigid two-photon absorbing polymers", Polymers for Advanced Technology (2005) 16: 150-155.
Tan, Loon-Seng; Srinivasan, K. R.; Bai, Shih Jung; Spry, Robert J. "New aromatic benzazole polymers II: synthesis and conductivity of benzobisthiazole-co-polymers incorporated with 4-N,N-dimethylaminotriphenylamine groups", Journal of Polymer Science, Part A: Polymer Chemistry (1998), 36(5), 713-724.
Jenekhe, Samson A.; Osaheni, John A.; Meth, Jeffrey S.; Vanherzeele, Herman, "Nonlinear optical properties of poly(p-phenylenebenzobisoxazole)", Chemistry of Materials, (1992) vol. 4, Issue 3, pp. 683-687.
Tan, Loon-Seng; Srinivasan, K. R.; Bai, Shih Jung, "New aromatic benzazole polymers I: Benzobisthiazole and benzobisoxazole polymers with main-chain triarylamino units", Journal of Polymer Science, Part A: Polymer Chemistry (1997), 35(10), 1909-1924.
Kannan, Ramamurthi; He, Guang S.; Yuan, Lixiang; Xu, Faming; Prasad, Paras N.; Dombroskie, Ann G.; Reinhardt, Bruce A.; Baur, Jeffery W.; Vaia, Richard A.; Tan, Loon-Seng "Diphenylaminofluorene-Based Two-Photon-Absorbing Chromophores with Various π -Electron Acceptors", Chemistry of Materials (2001), 13(5), 1896-1904.
Kazuo Haga, Katsumasa Iwaya, Ryohei Kaneko, "Condensation of 1,4-cyclohexanediones and secondary aromatic amines II: N-phenylation of diarylamines", Bulletin of the Chemical Society of Japan (1986), 59(3), 803-807.
Kannan, Ramamurthi; He, Guang S.; Lin, Tzu-Chau; Prasad, Paras N.; Vaia, Richard A.; Tan, Loon-Seng, "Toward Highly Active Two-Photon Absorbing Liquids. Synthesis and Characterization of 1,3,5-Triazine-Based Octupolar Molecules", Chemistry of Materials (2004), 16(1), 185-194.
He, Guang S.; Lin, Tzu-Chau; Dai, Jianming; Prasad, Paras N.; Kannan, Ramamurthi; Dombroskie, Ann G.; Vaia, Richard A.; Tan, Loon-Seng, "Degenerate two-photon-absorption spectral studies of highly two-photon active organic chromophores", Journal of Chemical Physics (2004), 120(11), 5275-5284.
Loon-Seng Tan, Matthew J Dalton, Rachel Jakubiak, Ramamurthi Kannan, Nikolay Makarov, Aleks Rebane, Augustine M Urbas, Thomas M Cooper, "Synthesis and Characterization of a Novel Film-Forming, Two-Photon Absorbing Benzobisthiazole Polymer and Related Model Compound", Abstract for poster presentation at "9th International Symposium on Functional Pi-Electron Systems" Conference, Georgia Institute of Technology, Atlanta, GA, May 23-28, 2010.
Agolini et al., "Synthesis and properties of azoaromatic polymers," Macromol., vol. 3 (1970) 349-351.
Chao et al., "Nonlinear optical polyimide/montmorillonite nanocomposites consisting of azobenzene dyes," Dyes and Pigments, vol. 77 (2008) 515-524.
Georgiev et al., "Polyimide coatings containing azo-chromophores as structural units," J. Phys.: Conf. Ser., vol. 113 (2008) 012032, 4 pages total.
Hosono et al., "Photochemical control of network structure in gels and photo-induced changes in their viscoelastic properties," Colloids and Surfaces B: Biointerfaces, vol. 56 (2007) 285-289.
Machine, Translation of JP 2005-154643, accessed Sep. 10, 2013, 39 pages total.
Koshiba et al., "Photo-induced alignment behavior of azobenzene compound in thin film," Thin Solid Films, vol. 518 (2009) 805-809.
Lee et al. "Relationship between the photomechanical response and the thermomechanical properties of azobenzene liquid crystalline polymer networks," Macromol., vol. 43 (2010) 8185-8190.
Lee et al., "Photomechanical response of composite structures built from azobenzene liquid crystal polymer networks," Polymers, vol. 3 (2011) 1447-1457.
Meador et al, "Synthesis and properties of nanoporous polyimide aerogels having a covalently bonded network structure," ACS Spring National Meeting, Mar. 1, 2011, 2 pages total.
Meador et al., "Improvements to the synthesis of polyimide aerogels," Polymer Preprints, vol. 51 (2010) 34 pages total.
Sakamoto et al, "Light exposure dependence of molecular orientation of glassy polyfluorene layers formed on photo-aligned polyimide films," Colloids and Surfaces B: Biointerfaces, vol. 56 (2007) 260-264.
Sakamoto et al., "Highly polarized polymer-based light-emitting diodes fabricated by using very thin photoaligned polyimide layers," J. Appl. Phys., vol. 107 (2010) 113108, 9 pages total.
Tyan et al., "Effect of reactivity of organics-modified montomorillonite on the thermal and mechanical properties of montmorillonite/polyimide nanocomposites," Chem. Mater., vol. 13 (2001) 222-226.
Usami et al., "Pretilt angle control of liquid crystal molecules by photoaligned films of azobenzene-containing polyimide with a different content of side-chain," J. Appl. Phys., vol. 104 (2008) 113528, 5 pages total.

(56) References Cited

OTHER PUBLICATIONS

Usami et al., "Improvement in photo-aligned efficiency of azobenzene-containing polyimide films," Thin Solid Films, vol. 518 (2009) 729-734.

Zhang et al., "Rapid bending of a nonliquid crystal azobenzene polymer film and characteristics of surface relief grating," J. Appl. Polym. Sci., vol. 113 (2009) 1330-1334.

United States Patent and Trademark Office, Non-Final Office Action in U.S. Appl. No. 13/475,159, mailed Aug. 14, 2012, 10 pages total.

United States Patent and Trademark Office, Non-Final Office Action in U.S. Appl. No. 13/661,194, mailed Jul. 2, 2014, 7 pages total.

United States Patent and Trademark Office, Non-Final Office Action in U.S. Appl. No. 13/546,439, mailed Nov. 7, 2013, 9 pages total.

United States Patent and Trademark Office, Non-Final Office Action in U.S. Appl. No. 13/866,551, mailed Feb. 10, 2014, 6 pages total.

Bell et al., "Polyimide structure-property relationships. II. Polymers from Isomeric diamines," J. Polym. Sci., vol. 14 (1976) 2275-2292.

Dalton et al., "Synthesis and characterization of novel aromatic imide polymer and co-polymers containing diphenylaminofluorene-benzothiazole as two-photon chromophoric units," Polymer Preprints, vol. 50 (2009) 495-496.

Siwy et al., "Novel poly(esterimide)s containing a push-pull type azobenzene moiety-synthesis, characterization and optical properties," Polym. J., vol. 40 (2008) 813-824.

\* cited by examiner ured into various, useful forms (films, coatings, fibers, windows, etc.) and configurations, should not be neglected. Furthermore, device fabrication and integration conditions should be considered in parallel with the continuing efforts to enhance the effective cross-section (a) values. For the aforementioned solid forms, polymers can offer many advantages such as the flexibility in fine-tuning the material properties, and the availability of many processing options.

TWO-PHOTON ABSORBING POLYMERS BASED ON TRIARYLAMINE-BENZOBISTHIAZOLE-TRIARYLAMINE QUADRUPOLAR-STRUCTURE MOTIF

CROSS REFERENCE TO RELATED APPLICATION

This application claims the benefit of and priority to the filing date of U.S. Provisional Application No. 61/487,774, filed May 19, 2011, and incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The present invention relates to benzobisthiazole-based polymers containing main-chain chromophores and having large, effective two-photon absorption cross-sections and high solubility in organic solvents.

BACKGROUND OF THE INVENTION

Multiphoton absorption ("MPA") is a nonlinear optical process that occurs through the simultaneous absorption of two or more photons via virtual states in an absorbing medium. Absorption of two photons is generally more common than absorption of more than two photons. For a given chromophore, the absorption processes take place at wavelengths much longer than the cut-off wavelength of its linear (single-photon) absorption. In the case of two-photon absorption (2PA), two quanta of photons may be absorbed from a single light source (referred to as degenerate 2PA or direct 2PA) or from two sources of differing wavelengths (referenced as non-degenerate 2PA). In practice, the former 2PA phenomenon is much more pervasive in two-photon applications. Thus, in considering the practical exploitation of a direct 2PA processes, it is important to recognize the following useful features of the 2PA phenomenon, which are based on the fact that 2PA scales nonlinearly with the squared intensity of the incident laser beam. Firstly, incident light at a low frequency (energy) may be upconverted to an output, emission light at higher frequency. For instance, near infrared ("NIR") may be upconverted to ultraviolet ("UV") via a 2PA upconversion process. The deeper penetration of incident NIR light than UV light that may be hazardous with prolonged exposure. Highly localized excitation via a 2PA process, as compared with one-photon processes, allows precise spatial control of in situ photochemical or photophysical events in the absorbing medium, thereby minimizing undesirable activities such as photodegradation or photobleaching. Finally, fluorescence (i.e., light emission via relaxation from singlet excited state to ground state) when properly manipulated, allow for information/signal feedback or amplification in conjunction with other possible, built-in effects, such as surface plasmonic enhancement effect.

It is anticipated that ingenious utilization of these basic characteristics of 2PA process will lead to practical applications beyond bio-medical fluorescence imaging, data storage, directed energy protection, hazardous chemical detection, microfabrication of microelectromechanical systems ("MEMS"), photodynamic therapy, etc. In the past two decades, significant advances have been made in the fundamental understanding of structure-property relationship of 2PA processes, which have led to the design and synthesis of two-photon absorbers having large cross-section values. While theoretical studies have suggested further enhancement of 2PA cross-section is still possible for certain applications, the two-photon-property requirement has essentially been met by state-of-art chromophores. Because of the possible property-processing/fabrication trade-off, optimization of secondary properties, e.g., thermal and mechanical properties, which are important in processing materials into vari- Aromatic-heterocyclic rigid-rod polybenzobisazoles ("PBXs"), such as polybenzobisthiazole ("PBZT"), polybenzobisoxazole ("PBO"), and polybenzobisimidazole ("PBI"), are well known for their superior thermal and mechanical properties and their promising nonlinear-optical ("NLO") and opto-electronic properties. These stiff-chain and fully conjugated polymers are typically synthesized in acidic media, such as polyphosphoric acid or methanesulfonic acid/phosphorus pentoxide mixtures. However, PBXs have the disadvantage that their practical solubility, which is limited to only strong acids. It is known to practitioners in the field that PBXs without suitable solubilizing pendants are practically insoluble, even at low molecular weights, in organic solvents commonly used in solution-based polymer processing. For structurally unmodified PBXs, such a drawback has constituted a serious problem in film fabrication and coating applications for NLO devices.

In U.S. Pat. No. 6,730,793, Ramamurthi Kannan et al., issued May 5, 2004, a suite of quadrupolar two-photon absorbing compounds based on a "Donor-Acceptor-Donor (D-A-D)" structural motif was described. Among these 2PA compounds were examples based on diphenylamine-benzobisthiazole-diphenylamine motif, which have high two-photon absorptivity. Traditionally, the formation of a benzene-fused bis(heterocycle), benzobisimidazole, benzobisoxazole or benzobisthiazole proceeded via a tandem condensation/dehydration process of a tetrafunctional monomer, i.e., 1,2,4,5-tetraaminobenzene, 4,6-diaminoresorcinol, or 2,5-diaminobenzene-1,3-thiol, respectively. A difunctional monomer, such as an aromatic dicarboxylic acid or acid chloride, drives the polymer-forming process. Viably, an alternative polymerization process entails a monomer comprising a preformed benzobis(heterocycle) structure with suitable reactive endgroups can engage in the formation of aryl-aryl bonds (as polymer-forming reaction) with a suitable co-monomer.

SUMMARY OF THE INVENTION

Accordingly, it is an object of the present invention to provide two-photon active monomers containing diphenylamine-benzobisthiazole-diphenylamine, i.e., a difunctionalized (X as reactive endgroup) benzobisthiazole monomer with the following generic structure:

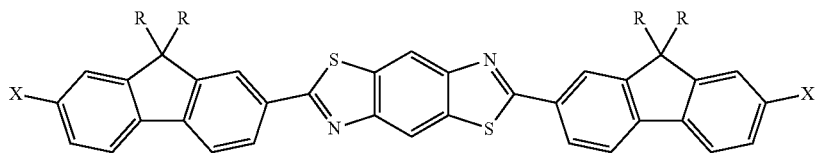

where R represents linear or branched alkyl chains having the formula $C_nH_{2n+1}$, where the subscript n ranges from 1 to 20; and X represents halides (preferably bromine or iodide), a trialkyltin (having the formula —$SnR'_3$, with preferably R' being an n-butyl), a triflate (having the formula —$OSO_2CF_3$).

Another object of the invention is to provide PBX-based polymers with repeating units and having a common structural motif. A benzobisthiazole core of the PBX-based polymer serves as an electron-accepting component (A), which is doubly connected to an electron-donating component (D) and tertiary amino endgroups via 9,9-dialkyfluorenyl bridges.

Concurrent to the second objective, another object of the present invention is to incorporate suitable solubilizing moieties to generate two-photon absorbing polymers that can be solution-processed into free-standing films and coatings using common organic solvents.

Another objective is to demonstrate the applicability of palladium-catalyzed reactions to polycondensate a dibromo monomer comprising a preformed benzobisthiazole moiety (e.g., compound 3 in Scheme 1) and a bis(boronate) monomer based on triphenylamine (compound 6 in Scheme 1) or other appropriately difunctionalized benzobisthiazole monomers in conjunction with dibromotriphenylamine.

In accordance with the present invention, there are provided two-photon active monomers containing diphenylamine-benzobisthiazole-diphenylamine, difunctionalized (X as reactive endgroup) benzobisthiazole monomer having the structure:

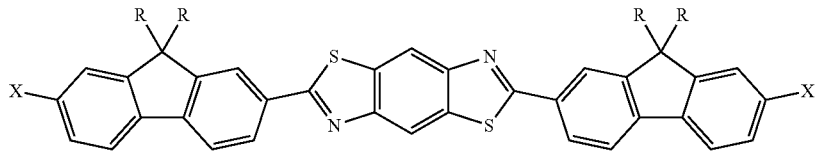

where R represents linear or branched alkyl chains having the formula $C_nH_{2n+1}$, where the subscript n ranges from 1 to 20, and X represents halides (preferably Br or I), trialkyltin (having the structure —$SnR'_3$ with R' being an n-butyl), or triflate (having the structure —$OSO_2CF_3$).

Also provided are the corresponding organo-soluble, wholly conjugated and two-photon absorbing benzobisthiazole-triarylamine polymers having the formula:

where R represents linear or branched alkyl chains having the formula $C_nH_{2n+1}$, where the subscript n ranges from 1 to 20. The subscript DP represents the degree of polymerization and may range from 10 to 100. As an illustration, these polymers are synthesized from palladium-catalyzed cross-coupling polymerization of one of the following combinations: (i) a benzobisthiazole-dialkylfluorenyl dibromo monomer and 4,4'-bis(boronato)triphenylamine via a Suzuki-Miyaura coupling reaction; (ii) a benzobisthiazole-dialkylfluorenyl bis (trialkyltin) monomer and 4,4'-dibromotriphenylamine via a Stille coupling reaction; and (iii) a benzobisthiazole-dialkylfluorenyl bis(aryl-O-sulfonate) monomer and 4,4'-dibromotriphenylamine, wherein O-sulfonate includes, but is not limited to, triflate (—O—$SO_2CF_3$) moiety.

Other objects and advantages of the invention will be set forth in part in the description, which follows, and, in part, will be obvious from the description, or may be learned by practice of the invention. The objects and advantages of the invention may be realized and attained by means of the instrumentalities and combinations particularly pointed out in the appended claims.

DETAILED DESCRIPTION

A method for the syntheses of the precursors and the corresponding monomers is shown, below, in Scheme 1. Briefly, the dibromo-benzobisthiazole monomer 3 was prepared in a 3-step sequence starting from commercially-available 2,7-dibromofluorene. The 2,7-dibromofluorene was dialkylated with a bromoalkane (e.g. 1-bromo-3,7-dimethyloctane) in the presence of KOH/KI in dimethyl sulfoxide (DMSO). There are multiple purposes of having the branched alkyl sidechains (3,7-dimethyloctyl) in monomer 3, namely to: (a) promote solubility during polymerization, (b) increase ease of film fabrication, and (c) frustrate the aggregation of the benzobisthiazole-fused structure in the solid-state (cast film).

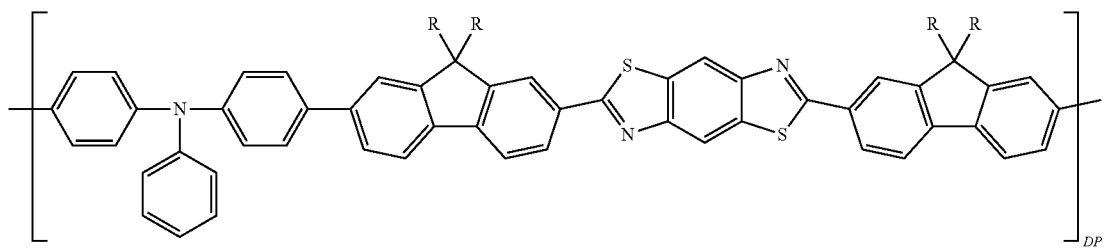

The diboronate-functionalized triphenylamine monomer 6 was prepared from the corresponding dibromotriphenylamine 4, by lithiation with n-butyllithium, followed by borylation with isopropoxydioxaborolane. To eliminate the need to separate mixtures of brominated products resulting from directly brominating triphenylamine, dibromotriphenylamine was cleanly prepared by an unusual condensation of 4,4'-dibromodiphenylamine and cyclohexanedione, as taught by KAZUO HAGA et al., "Condensation of 1,4-cyclohexanediones and secondary aromatic amines II: N-phenylation of diarylamines," Bull. Chem. Soc. Japan., Vol. 59 (1986) 803-807, the disclosure of which is incorporated herein by reference in its entirety.

phase-transfer agent in aqueous toluene. The resulting polymer was characterized by $^1$H and $^{13}$C NMR, mass spectrometry ("MALDI-MS"), elemental analysis, and thermal analysis ("TGA/DSC"), and the expected molecular structures are confirmed by these characterization data. In addition, the endgroup protons can clearly be seen in the $^1$H-NMR spectrum of the polymer and were used to calculate molecular weight with the aid of MALDI-MS data. Careful analysis of the masses of the monomers, dimers, and trimers revealed that the majority were terminated with two phenylated-triphenylamine moieties. These endgroups were a result of phenyl transfer from the catalyst to the arylboronate and suggest this was the primary path of termination. This implies that using Scheme 1: Synthesis of bis(boronate) monomer

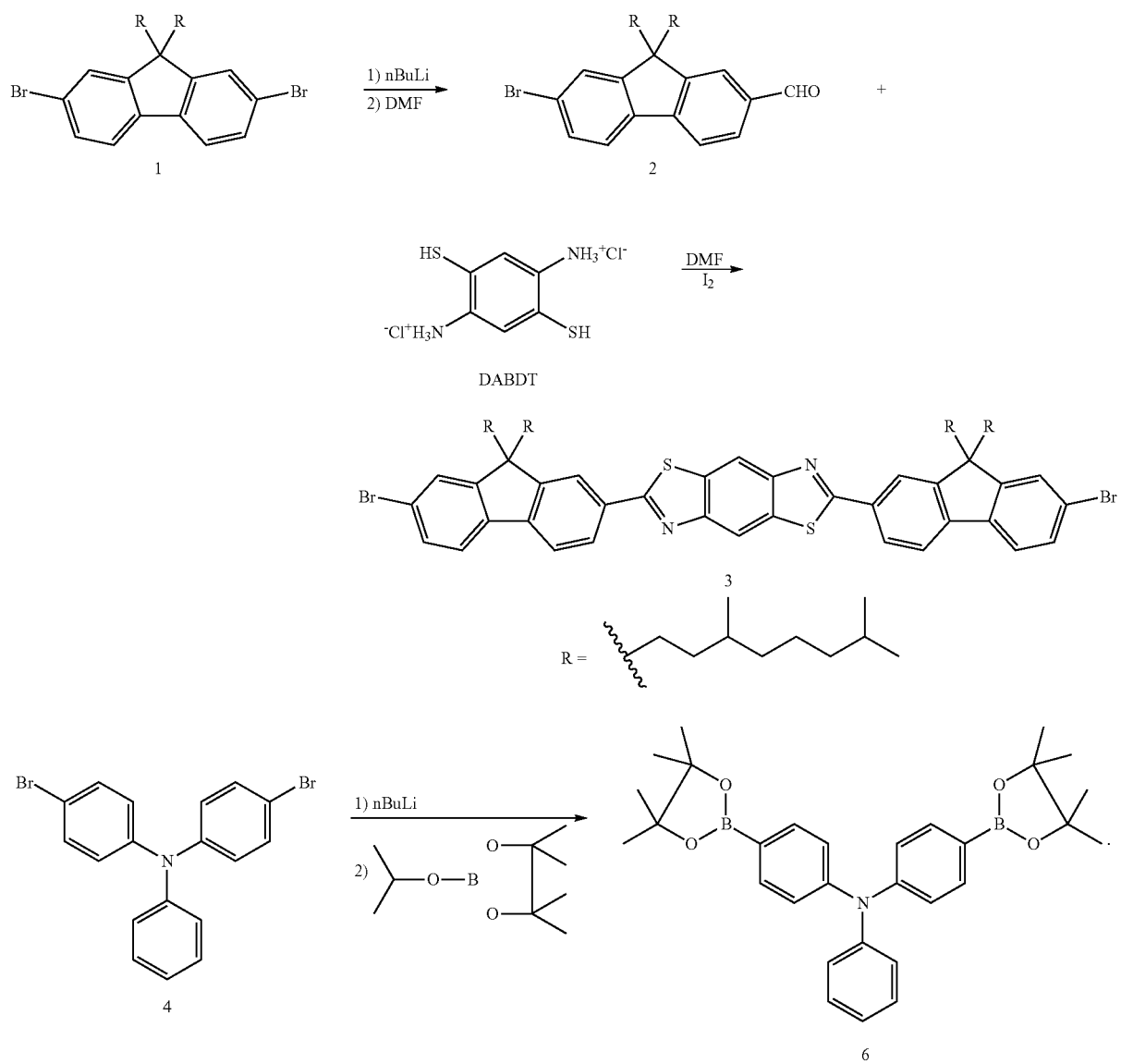

A representative, two-photon active benzobisthiazole polymer was prepared according to the method depicted, below, in Scheme 2. Suzuki polycondensation was employed to prepare the polymer and was effected by the use of about 2 mol % Pd(PPh$_3$)$_4$ as the catalyst, sodium carbonate, and a less catalyst should allow for higher degrees of polymerization. Assuming the majority of all chains were terminated in a similar fashion allowed for the calculation of a number-average molecular weight ($M_n$) of 13.2 kDa, based on integration of the respective peak area in the proton spectrum.

Scheme 2: A representative scheme for the preparation of two-photon active benzobisthiazole polymers via Suzuki reaction

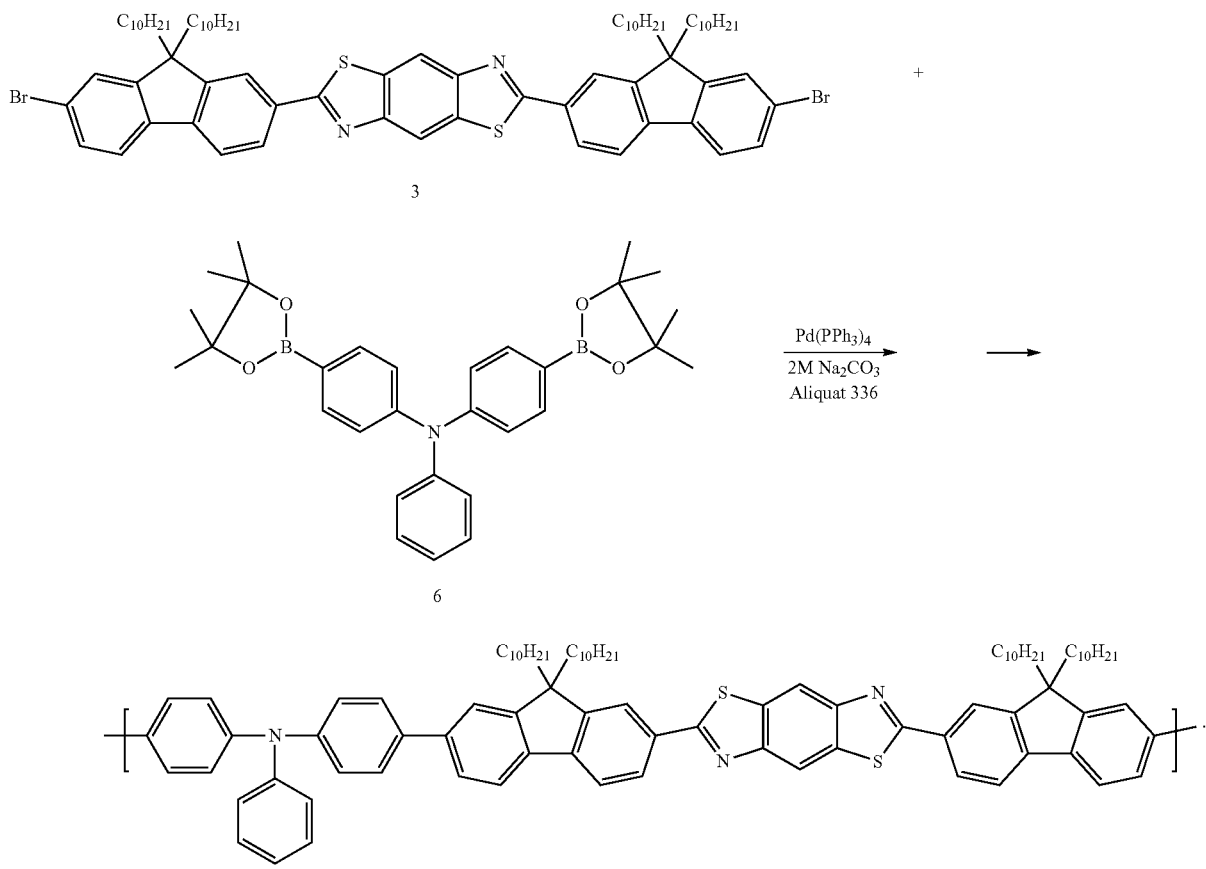

The two-photon active benzobisthiazole polymer was readily soluble in most organic solvents, including chloroform, toluene, and THF. The polymer could also be cast into an optically-clear film with reasonable mechanical properties.

The organo-soluble benzobisthiazole-triphenylamine-based monomers and polymers of this invention can be synthesized by procedures given in the following Examples, which illustrate the invention:

Example 1

2,7-Dibromofluorene

To a mechanically stirred mixture of fluorene (113.76 g., 0.68 mol), iodine (1.96 g., 0.0077 mol), and methylene chloride (750 mL), bromine (74 mL, 1.44 mol) diluted with methylene chloride (100 mL) was added dropwise at room temperature over a period of 1.5 hours. After 5 minutes, a solution of sodium bisulfite (15.0 g) in water (100 mL) was added, and the mixture was stirred for 30 minutes, at which time the mixture became colorless. Water (750 mL) was then added, and methylene chloride was distilled off. The product slurry was filtered and the product was air-dried, 220.5 g., m.p. 151 (sh), 156-160° C. This material was used in the next step without further purification.

Example 2

Racemic dihydrocitronellyl bromide (1-bromo-3,7-dimethyloctane)

Concentrated sulfuric acid (17 mL) was added to 48% hydrobromic acid (100 mL) with stirring. 3,7-dimethyloctanol (dihydrocitronellol, Aldrich, 67 mL, 100 g) was then added to the mixture. The mixture was then heated to 120-125° C., and kept at this temperature for 3 hours. The reaction was cooled and extracted into heptane (300 mL). The heptane layer was washed with a hydrochloric acid, water, and sodium bicarbonate solution, dried, and concentrated to leave an oil, 81.5 g. This oil was distilled under vacuum at a bath temperature of 120-125° C. to afford the bromide product as an oil, b.p. 85-87° C./10 mmHg, 78.2 g, 100% yield. Mass Spec: m/z 220, 222 (M$^+$).

Example 3

Racemic and meso-9,9-bis(3,7-dimethyloctyl)-2,7-dibromofluorene

To a mechanically stirred mixture of 2,7-dibromofluorene (58.32 g, 0.18 mol), potassium iodide (3.0 g, 18 mmol), potassium hydroxide (50.4 g, 0.9 mol) and DMSO (150 mL) cooled in ice-water to 15° C., dihydrocitronellyl bromide (86.8 g, 0.392 mol) was added. The mixture was stirred at room temperature for 18 hours. The mixture was poured into water, and the product extracted into a mixture of 1:1 toluene-heptane. The organic phase was washed with water, dried, and concentrated. The residual oil was refluxed with pyridine for 18 hours to quarternize any unreacted dihydrocitronellyl bromide, and the mixture was diluted with toluene-heptane. The organic phase was washed with water, dried, and concentrated. The residual orange oil was transferred to a column of 1050 g of alumina. Elution with hexanes (1800 mL) gave the product, 102.25 g, 94% yield, as a colorless oil. Mass Spec: m/z 602, 604, 606 (M+). Anal. Calcd. for $C_{33}H_{48}Br_2$: C, 65.56%; H, 8.00%; Br, 26.44%. Found: C, 65.80%; H, 7.81%; Br, 26.30%.

Example 4

7-Bromo-9,9-bis(3,7-dimethyloctyl)-9H-fluorene-2-carbaldehyde

To a flame-dried, 3-neck, round-bottomed flask equipped with mechanical stirring and an addition funnel was added the mixture of racemic and meso-9,9-bis(3,7-dimethyloctyl)-2,7-dibromofluorene, which had been obtained in Example 3 (79.3 g, 131.2 mmol), and THF (350 mL) by cannula. The solution was cooled to −78° C. and 2.5M n-BuLi in hexane (52.5 mL, 131.2 mmol) was added via the addition funnel over 15 min. After stirring for 30 min, dimethylformamide (20.0 mL, 262 mmol) in THF (30 mL) was added dropwise. The reaction mixture was allowed to warm to room temperature overnight. Toluene and water were added, and the organic phase was further washed with water, dried with $MgSO_4$, and concentrated. The crude product was purified by column chromatography, eluting with heptane to 20% toluene/heptane to give 54 g (75%)

$^1$H NMR (400 MHz, $CDCl_3$) δ ppm: 10.06 (s, 1H), 7.88-7.79 (m, 3H), 7.63 (m, 1H), 7.51 (m, 2H), 1.41 (m, 2H), 1.20-0.93 (m, 12H), 0.92-0.75 (m, 14H), 0.66 (m, 6H), 0.60-0.30 (m, 4H); $^{13}$C NMR (100 MHz, $CDCl_3$) δ ppm: 192.07, 154.09, 150.98, 146.32, 138.51, 135.52, 130.36, 126.27, 123.02, 122.13, 120.00, 55.32, 38.99, 37.29, 37.23, 36.40, 32.62, 31.79, 30.26, 27.79, 24.45, 24.39, 22.55, 22.46, 19.32, 14.02. δ El-MS (m/z): 552, 554 (M+). Anal. Calcd. for $C_{34}H_{49}BrO$: C, 73.76%; H, 8.92%; Br, 14.43%. Found: C, 73.80%; H, 8.86%; Br, 14.64%.

Example 5

2,6-Bis(7-bromo-9,9-didecyl-9H-fluoren-2-yl)benzo[1,2-d; 4,5-d]bisthiazole

To a solution of 7-bromo-9,9-bis(3,7-dimethyloctyl)-9H-fluorene-2-carbaldehyde (obtained in Example 4; 31.15 g, 56.3 mmol) in DMF (145 mL) were added 2,5-diaminobenzene-1,4-dithiol (DABDT; 6.90 g, 28.1 mmol), tributylamine (15 mL, 62 mmol), and iodine pellets (7.14 g, 28.13 mmol). The red solution was heated at 105° C. for 5 hr. After cooling, additional tributylamine (15 mL, 62 mmol) was added, and the precipitate was filtered and washed with methanol (250 mL). The crude product was then purified by column chromatography eluting with heptane to 50% toluene/heptane followed by crystallization from heptane to give 15.6 g (45%). mp. 153-154° C.

$^1$H NMR (400 MHz, $CDCl_3$) δ ppm: 8.57 (s, 2H), 8.09 (m, 4H), 7.77 (d, J=7.8 Hz, 2H), 7.61 (m, 2H), 7.49 (m, 4H), 2.20-1.95 (m, 8H), 1.39 (m, 4H), 1.20-0.82 (m, 28H), 0.80-0.73 (m, 24H), 0.70 (m, 12H), 0.62 (m, 4H), 0.49 (m, 4H); $^{13}$C NMR (100 MHz, $CDCl_3$) δ ppm: 169.26, 153.58, 152.27, 151.21, 143.37, 139.15, 134.42, 132.60, 130.27, 127.21, 126.25, 122.22, 121.68, 120.29, 115.12, 76.68, 55.59, 39.14, 37.46, 36.53, 36.48, 32.78, 30.43, 30.36, 27.91, 27.88, 24.54, 24.52, 22.63, 22.55, 22.52, 19.51, 19.44. El-MS (m/z): 552, 554 (M+). Anal. Calcd. for $C_{74}H_{98}N_2S_2Br_2O$: C, 71.70%; H, 7.97%; Br, 12.89%; N, 2.26%; S, 5.17%. Found: C, 71.79%; H, 7.99%; Br, 12.82%; N, 2.33%; S, 5.15%.

Example 6

4,4'-Dibromotriphenylamine

A mixture of 4,4'-dibromodiphenylamine (7.3 g. 22 mmol), cyclohexane-1,4-dione (2.5 g., 23.3 mole), para-toluenesulfonic acid (0.1 g.), and toluene (100 mL) was kept at reflux with a Dean-Stark 15 phase separator containing 4A molecular sieves. After 18 hours at reflux, the reaction was diluted with toluene, and the toluene solution was washed with water, dried, and concentrated. The residue was dissolved in hexanes, and the hexanes solution was then passed through a column of silica gel to afford 4,4'-dibromotriphenylamine as a colorless glass, 5.04 g., 67% yield. Mass Spec (m/z): 401, 403, 405 (M+).

Example 7

Bis-[N,N'-phenyl-4-(4,4,5,5-tetramethyl-1,3,2-dioxaborolan-2-yl)]aniline

To a flame-dried 3NRBF equipped with mechanical stirring and an addition funnel was added 4,4'-dibromotriphenylamine (13.97 g, 34.7 mmol), LiCl (4.41 g, 104 mmol), and THF (250 mL) by cannula. The solution was cooled to −78° C. and 1.6 M n-BuLi in hexane (52 mL, 83.2 mmol) was added by addition funnel over 15 min. After stirring for 30 min, 2-isopropoxy-4,4,5,5-tetramethyl-1,3,2-dioxaborolane (17.7 mL, 86.6 mmol) in THF (15 mL) was added dropwise, and the reaction mixture was allowed to stir for 3 hr as it came to room temperature. Saturated $NH_4Cl$ (25 mL) and water (100 mL) were added and the majority of THF was removed by rotary evaporation. The crude product was dissolved in boiling isopropanol, hot-filtered, and crystallized to give 5.4 g (31%). The material was further purified by recrystallization from diethylether. mp. 268-270° C.

$^1$H NMR (400 MHz, $CDCl_3$) δ 7.67 (d, J=8.4 Hz, 4H), 7.26 (m, 2H), 7.10 (m, 3H), 7.06 (d, J=8.5 Hz, 4H) 1.34 (s, 24H); $^{13}$C NMR (100 MHz, $CDCl_3$) δ ppm: 150.10, 147.01, 135.86, 129.35, 125.58, 123.87, 122.71, 83.60, 24.84. El-MS (m/z): 497 (M+). Anal. Calcd. for $C_{30}H_{37}B_2NO_4$: C, 72.46%; H, 7.50%; B, 4.35%; N, 2.82%. Found: C, 72.45%; H, 7.55%; B, 4.39%; N, 2.66%.

Example 8

2PA-active benzobisthiazole polymer derived from the polymerization of bis-[N,N'-phenyl-4-(4,4,5,5-tetramethyl-1,3,2-dioxaborolan-2-yl)aniline] and 2,6-bis (7-bromo-9,9-didecyl-9H-fluoren-2-yl)benzo[1,2-d; 4,5-d']bisthiazole A reaction mixture of bis-[N,N'-phenyl-4-(4,4,5,5-tetramethyl-1,3,2-dioxaborolan-2-yl)]aniline (Example 7; 300.9 mg, 0.605 mmol), 2,6-bis(7-bromo-9,9-didecyl-9H-fluoren-2-yl)benzo[1,2-d; 4,5-d]bisthiazole (obtained in Example 5; 750 mg, 0.605 mmol), toluene (20 mL), 2 M $Na_2CO_3$ (3 mL), and a few drops of Aliquat 336 was degassed by argon bubbling for 20 min. $Pd(PPh_3)_4$ (14 mg, 0.0121 mmol) was then added, and the mixture was placed in a thermostated oil bath at 90° C. for 116 hr. Upon cooling to room temperature, the solution was poured into isopropanol (200 mL) to precipitate a fibrous yellow solid. The isopropanol was decanted and replaced with hot water. The solid was then filtered, washed with acetone, and dried. Re-precipitation from a 0.45 μm-syringe-filtered-solution of chloroform (40 mL) into acetone and drying gave 0.65 g (81%).

$^1$H NMR (400 MHz, CDCl$_3$) δ ppm: 8.59 (s, 2H), 8.12 (m, 4H), 7.83 (m, 4H), 7.61 (m, 8H), 7.33 (m, 2H) 7.24 (m, 6H) 7.10 (t, J=7.3 Hz, 1H), 2.15 (m, 8H), 1.39 (m, 4H), 1.22-0.50 (br, 72H); $^{13}$C NMR (100 MHz, CDCl$_3$) δ: 169.50, 152.32, 152.19, 151.81, 147.45, 147.08, 144.32, 140.53, 139.11, 135.65, 134.43, 132.13, 129.42, 127.95, 127.17, 125.84, 124.73, 124.20, 123.33, 121.74, 120.98, 120.66, 120.16, 115.04, 55.37, 39.19, 37.60, 36.69, 36.53, 32.87, 30.59, 30.52, 27.91, 27.88, 24.60, 22.63, 22.54, 22.52, 19.61, 19.49. Anal. Calcd. for C$_{92}$H$_{111}$N$_3$S$_2$: C, 83.52%; H, 8.46%; N, 3.18%; S, 4.85%. Found: C, 82.68%; H, 8.47%; N, 3.46%; S, 4.68%.

Example 9

Two-Photon Properties of Polymer Solution and Neat Film

A solution of the 2PA-active polymer (obtained in Example 8, 100 mg) was dissolved in chloroform (10 mL) and filtered through a 0.2 μm syringe filter into a flat-bottomed Pyrex dish (5 cm diameter) with a petri dish on top and left overnight. The film was soaked in water to remove from the glass and dried in a 90° C. oven overnight.

The film density was determined by cutting a small sample (4.0 mm×15.0 mm) of the film and measuring the thickness with a micrometer to 40±1 μm. The sample was weighed on a microbalance to 2.8±0.1 mg. These values were used to roughly estimate the density as 1.15±0.05 g/cm$^3$.

The two-photon activity of the polymer (obtained in Example 8) at 800 nm in THF solution (0.02 M) and as a neat film (40 μm thick; density=1.15 g·cm$^{-3}$) was confirmed under femtosecond-pulsed laser excitation by a standard open-aperture Z-scan experiment, and the intrinsic 2PA cross-section (σ$_2$') was determined. Thus, σ$_2$' values in solution and solid state were 119±4 and 69±4 GM per repeat unit, respectively (1 GM=10$^{-50}$ cm$^4$·sec/photon).

In addition, femtosecond two-photon-induced fluorescence (TPIF) method was also used to generate the two-photon spectrum for the subject polymer in THF solution (10$^{-5}$ M) covering the range from about 600 nm to 900 nm. It was found that the peak value was 1,600 GM at about 760 nm and the value at 800 nm value was about 800 GM.

Having thus described exemplary embodiments of the present invention, it should be noted by those skilled in the art that the disclosures herein are exemplary only and that alternatives, adaptations and modifications may be made within the scope of the present invention.

We claim:

1. A difunctionalized benzobisthiazole monomer having the following structure:

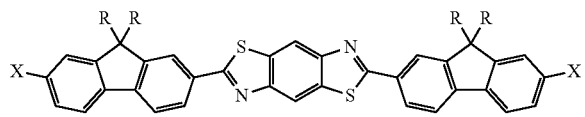

Wherein each R represents linear or branched alkyl chains having the formula C$_n$H$_{2n+1}$, of which the subscript n may range from 1 to 20; and X represents a functional group and each X is separately selected from the group consisting of halides, trialkyltin, triflate, and mixtures thereof.

2. The difunctionalized (X) benzobisthiazole monomer of claim 1, wherein the subscript n ranges from 10 to 15.

3. The difunctionalized (X) benzobisthiazole monomer of claim 1 wherein X is a halide.

4. The difunctionalized (X) benzobisthiazole monomer of claim 3 wherein X is Br or I.

5. A two-photon active benzobisthiazole-triarylamine polymer having the following structure:

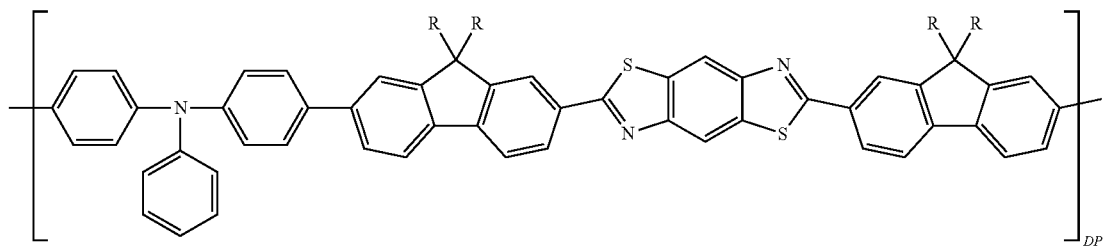

wherein R represents linear or branched alkyl chains having the formula C$_n$H$_{2n+1}$, of which the subscript n ranges from 1 to 20; and DP represents a degree of polymerization, which may range from 10 to 100.

6. The two-photon active benzobisthiazole-triarylamine polymer of claim 5 wherein the subscript n ranges from 10 to 15.

7. A two-photon active benzobisthiazole-triarylamine polymer comprising:
    a plurality of monomers comprising:
        the difunctionalized benzobisthiazole monomer of claim 1; and
        a di(N)triphenylamine, wherein N is a halide.

8. A method of polymerizing the difunctionalized benzobisthiazole monomer of claim 1, the method comprising:
    introducing a di(N)triphenylamine, wherein N is a halide; and
    coupling the difunctionalized benzobisthiazole monomer to the di(N)triphenylamine via a Suzuki-Miyaura reaction.

9. A method of polymerizing the difunctionalized benzobisthiazole monomer of claim 1, the method comprising:
    introducing a di(N)triphenylamine, wherein N is a halide; and
    coupling the difunctionalized benzobisthiazole monomer to the di(N)triphenylamine via a Stille reaction.

* * * * *